(12) United States Patent
McGrath

(10) Patent No.: US 11,517,193 B2
(45) Date of Patent: Dec. 6, 2022

(54) LARYNGOSCOPE BLADE

(71) Applicant: COVIDIEN AG, Neuhausen am Rheinfall (CH)

(72) Inventor: Matthew McGrath, Edinburgh (GB)

(73) Assignee: COVIDIEN AG, Neuhausen am Rheinfall (CH)

( * ) Notice: Subject to any disclaimer, the term of this patent is extended or adjusted under 35 U.S.C. 154(b) by 0 days.

(21) Appl. No.: 15/604,105

(22) Filed: May 24, 2017

(65) Prior Publication Data
US 2017/0258313 A1    Sep. 14, 2017

Related U.S. Application Data

(63) Continuation of application No. 14/753,835, filed on Jun. 29, 2015, now Pat. No. 9,693,677, which is a continuation of application No. 12/086,245, filed as application No. PCT/GB2006/004608 on Dec. 11, 2006, now Pat. No. 9,066,700.

(51) Int. Cl.
| | |
|---|---|
| *A61B 1/267* | (2006.01) |
| *A61B 1/00* | (2006.01) |
| *A61B 1/04* | (2006.01) |
| *A61B 1/06* | (2006.01) |
| *A61B 1/07* | (2006.01) |

(52) U.S. Cl.
CPC ........ *A61B 1/2673* (2013.01); *A61B 1/00096* (2013.01); *A61B 1/00101* (2013.01); *A61B 1/00135* (2013.01); *A61B 1/00174* (2013.01); *A61B 1/04* (2013.01); *A61B 1/0623* (2013.01); *A61B 1/07* (2013.01); *A61B 1/267* (2013.01); *A61B 1/00142* (2013.01); *A61B 1/0676* (2013.01)

(58) Field of Classification Search
CPC .................................................. A61B 1/00–32
See application file for complete search history.

(56) References Cited

U.S. PATENT DOCUMENTS

| | | | |
|---|---|---|---|
| 3,005,452 A | 10/1961 | Pitman et al. | |
| 3,643,654 A * | 2/1972 | Felbarg | A61B 1/267 |
| | | | 359/857 |

(Continued)

FOREIGN PATENT DOCUMENTS

| | | |
|---|---|---|
| EP | 1031315 A1 | 8/2000 |
| FR | 2830429 A1 | 4/2003 |

(Continued)

OTHER PUBLICATIONS

Chinese Office Action & Search Report; Application No. 201501823312.7, dated Sep. 8, 2016.

(Continued)

*Primary Examiner* — Eduardo C Robert
*Assistant Examiner* — Steven J Cotroneo

(57) ABSTRACT

A laryngoscope blade which improves the transmission of light from the laryngoscope to enhance the amount of light reflected from an area of interest in a patient. The laryngoscope blade has a channel which extends at least partially though the blade and receives a light source. The channel has a substantially transparent end face which is situated towards the blade end and has an optical clement adapted to reduce the ambient light signal from the light source in the channel.

22 Claims, 6 Drawing Sheets

(56) References Cited

U.S. PATENT DOCUMENTS

| | | | |
|---|---|---|---|
| 4,611,579 A * | 9/1986 | Bellhouse | A61B 1/267 600/189 |
| 4,660,982 A * | 4/1987 | Okada | A61B 1/00096 356/636 |
| 4,802,460 A * | 2/1989 | Ohkuwa | A61B 1/00096 385/117 |
| 5,193,525 A | 3/1993 | Silverstein et al. | |
| 5,196,525 A | 3/1993 | McPherson et al. | |
| 5,603,688 A * | 2/1997 | Upsher | A61B 1/2676 600/185 |
| 5,718,663 A | 2/1998 | Wulfsberg | |
| 5,873,818 A | 2/1999 | Rothfels et al. | |
| 6,106,458 A | 8/2000 | Ha et al. | |
| 6,115,523 A | 9/2000 | Gravenstein et al. | |
| 6,142,144 A * | 11/2000 | Pacey | A61B 1/267 128/200.26 |
| 6,364,830 B1 * | 4/2002 | Durell | A61B 1/00183 600/129 |
| 6,503,196 B1 | 1/2003 | Kehr et al. | |
| 6,655,377 B2 | 12/2003 | Pacey | |
| 6,676,598 B2 | 1/2004 | Rudischhauser et al. | |
| 6,680,800 B1 | 1/2004 | Schreiber et al. | |
| 6,843,769 B1 * | 1/2005 | Gandarias | A61B 1/0676 600/185 |
| 7,044,909 B2 | 5/2006 | Berci et al. | |
| 7,175,593 B2 * | 2/2007 | Durell | A61B 1/00165 600/130 |
| 7,341,556 B2 | 3/2008 | Shalman | |
| 7,608,040 B1 | 10/2009 | Dunst | |
| 7,744,529 B2 | 6/2010 | Sakamoto | |
| 7,824,331 B1 | 11/2010 | Cranton et al. | |
| 7,946,981 B1 * | 5/2011 | Cubb | A61B 1/00052 600/120 |
| 2001/0014768 A1 | 8/2001 | Kaplan et al. | |
| 2002/0087050 A1 | 7/2002 | Rudischhauser et al. | |
| 2003/0032864 A1 | 2/2003 | Friesen | |
| 2003/0088156 A1 | 5/2003 | Berci et al. | |
| 2003/0181789 A1 | 9/2003 | Mazzei et al. | |
| 2003/0195390 A1 | 10/2003 | Graumann | |
| 2004/0019256 A1 | 1/2004 | Cubb et al. | |
| 2005/0059863 A1 | 3/2005 | Zilch | |
| 2005/0159649 A1 | 7/2005 | Patel | |
| 2005/0192481 A1 | 9/2005 | Berci et al. | |
| 2006/0004260 A1 | 1/2006 | Boedeker et al. | |
| 2006/0020171 A1 | 1/2006 | Gilreath | |
| 2006/0020172 A1 | 1/2006 | Luerssen et al. | |
| 2006/0189847 A1 | 8/2006 | Yee et al. | |
| 2006/0247497 A1 | 11/2006 | Gardner | |
| 2006/0276694 A1 | 12/2006 | Acha Gandarias | |
| 2007/0093693 A1 | 4/2007 | Geist et al. | |
| 2007/0106121 A1 * | 5/2007 | Yokota | A61B 1/00052 600/188 |
| 2007/0106122 A1 * | 5/2007 | Yokota | A61B 1/00048 600/188 |
| 2007/0112257 A1 | 5/2007 | Hensler | |
| 2007/0129607 A1 | 6/2007 | Ashfaque | |
| 2007/0167686 A1 | 7/2007 | McGrath | |
| 2007/0179342 A1 | 8/2007 | Miller et al. | |
| 2007/0197873 A1 | 8/2007 | Birnkrant | |
| 2007/0299313 A1 | 12/2007 | McGrath | |
| 2009/0299146 A1 | 12/2009 | McGrath | |

FOREIGN PATENT DOCUMENTS

| | | |
|---|---|---|
| JP | 02033120 A | 2/1990 |
| JP | 02132409 A | 5/1990 |
| JP | 08252213 A | 10/1996 |
| JP | 2001292956 A | 10/2001 |
| JP | 2001292958 A | 10/2001 |
| JP | 2004049793 A | 2/2004 |
| WO | 2004096032 A1 | 11/2004 |

OTHER PUBLICATIONS

Examination Report issued in corresponding European Application No. 06831372.5 dated Feb. 14, 2014.
International Search Report for PCT/GB2006/004608 dated Jun. 13, 2007.

* cited by examiner

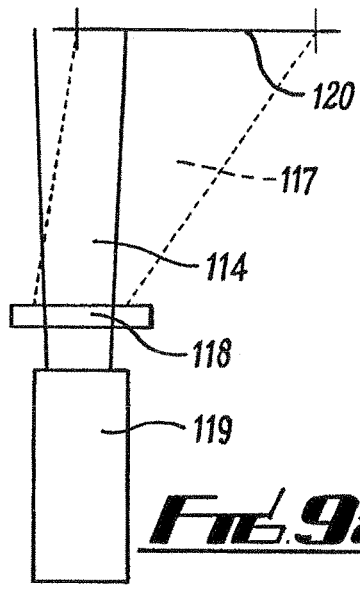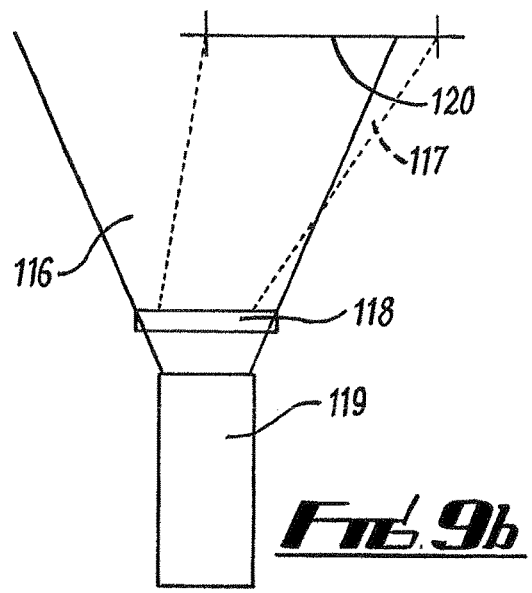
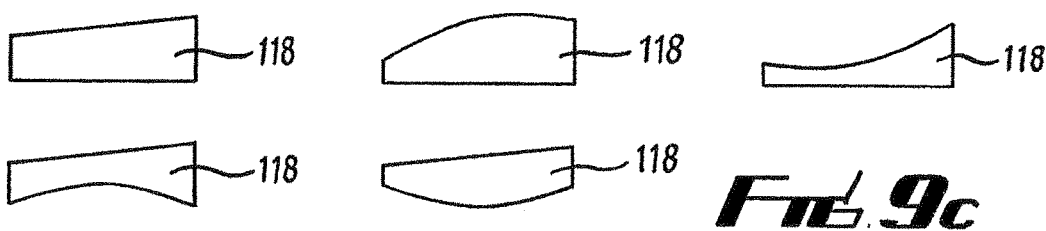
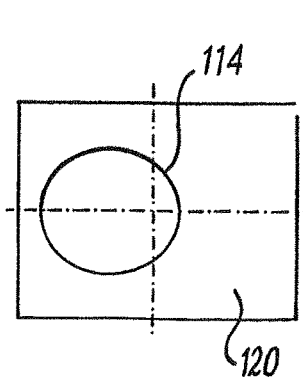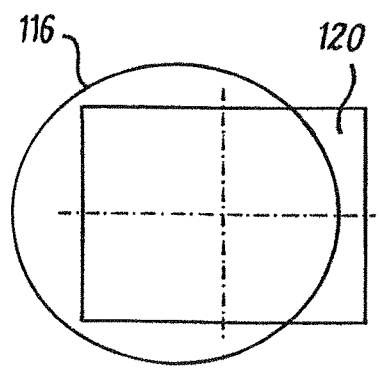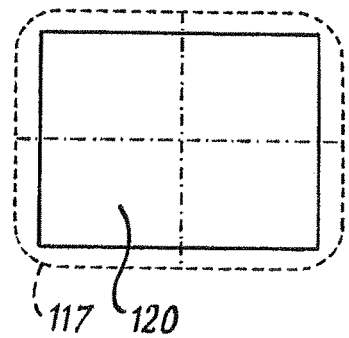

LARYNGOSCOPE BLADE

This application is a continuation of U.S. patent application Ser. No. 14/753,835 filed Jun. 29, 2015, which is a continuation of U.S. patent application Ser. No. 12/086,245, filed Jun. 9, 2008, which is a U.S. national phase of International Application No. PCT/GB2006/004608 filed Dec. 11, 2006, which designated the U.S. and claims priority to British Patent Application Nos. 0525095.6 filed Dec. 9, 2005 and 0525085.7 filed Dec. 9, 2005, the entire contents of each of which are hereby incorporated by reference.

The present invention relates to sheath type laryngoscopes and in particular to blades including disposable blades for said laryngoscopes.

The laryngoscope is a device that is used by physicians to open-up a patient's airway during the intubation process. One key aspect of the use of a laryngoscope is that the physician must be able to identify the vocal cords and surrounding anatomy when the laryngoscope is inserted. In most cases, this is done by visual identification of the larynx area by looking directly into the patient's mouth or by viewing that area on a video screen by having a camera positioned on, or within, the laryngoscope blade.

In general it is known to fit a light source to the outside of a non disposable laryngoscope blade. In addition some disposable laryngoscope blades consist of a sheath type blade with a transparent section that allows transmission of light from an end face into the throat of the patient. The light is intended to illuminate the anatomy so that a medic can see, or for an imaging system to capture an image. The advantage of a sheath is that the imaging and/or light source is protected from contact with the patient and is therefore better protected from patient to patient cross infection. Another advantage is that the relatively expensive camera and/or light source forms part of the reusable portion of the device, keeping the disposable sheath portion free from electronics and precious metals, which enables a cost effective and environmentally friendly solution.

One problem with the use of light sources mounted inside a sheath-type laryngoscope blade is that the light must transfer through the substantially transparent end face of the blade (or sheath) and can be reflected or otherwise leak into the sheath to cause a polluting ambient light signal, or scattering light. In addition, the scattered light means that not all of the light from the light source reaches the intended area in the patient's throat to provide a useful signal.

The problem is made worse by using light sources which provide a wide field of light that spreads to a wider area than the intended area of illumination. The wide angle causes the light to spread into the sheath instead of travelling through the sheath directly and efficiently. Additionally, the amount of light reaching the desired target area is diluted. A narrow beam of light will travel through the sheath window efficiently, with less scattering, but will often not allow a wide enough field of illumination on the target area.

A related problem with the illumination of the internal anatomy for the purpose of imaging for viewing on an external monitor is that the light source creates a circular field of illumination, like a cone of light, which is not optimal for current monitors which are rectangular rather than circular. Current systems therefore offer a circular spot of light within the frame of the monitor, or illuminate a wider circle of light beyond the frame of the monitor, which means light is wasted illuminating anatomy that is not displayed on the viewing monitor.

Medical probes for internal examination of the anatomy, such as laryngoscope blades, are often used alongside additional apparatus also inserted into the body. In the case of a laryngoscope blade a tracheal tube is passed into the patient's airway through the vocal cords. This means that it is preferable to have the laryngoscope blade positioned to one side (usually the left) to provide a space for the tube to be inserted. This means that the image capture and/or illumination means are offset to the target area, and therefore must be angled to the target area which can add complexity, cost and often results in bulkier packaging.

It is an object of the present invention to improve the operation of a laryngoscope by improving the transmission of light from the laryngoscope to enhance the amount of light reflected from an area of interest in a patient.

In accordance with the first aspect of the present invention there is provided a laryngoscope blade for a sheath type laryngoscope, the blade comprising:
 a hilt;
 a blade end; and
 a channel extending at least partially though the blade and being adapted to receive a light source, the channel having a substantially transparent end face situated towards the blade end and the end face comprising an optical element adapted to reduce the ambient light signal from the light source in the channel.

The blade end is the distal end with respect to the hilt. Also, the ambient light signal includes any scattered light.

Preferably, the blade further comprises an opening. Advantageously the opening is located at or near the hilt.

Preferably, the optical element is shaped to reduce the back scatter of light into the channel.

Preferably, the end face contains a castellation such that the position of the end face from which the light is emitted is in front of the remainder of the end face.

Preferably, the optical element is bounded at least in part by a channel.

Preferably, the optical element is adapted to redirect the beam of light.

Preferably, the optical element is adapted to spread the beam of light. Alternatively, the optical element is adapted to focus the beam of light.

Preferably, the optical element comprises a refractive means.

Preferably, and advantageously, the optical element is adapted to shape the beam of light so as to have a substantially rectangular cross section.

Optionally, the optical element comprises a prism.

Preferably, the optical element is adapted to receive a narrow beam of light and to broaden out the beam.

Preferably, the optical element further comprises a lens.

Optionally, the lens is a concave lens.

Optionally, the lens is a convex lens.

Preferably, the optical element is adapted to absorb light incident upon its side face.

Optionally, the optical element is adapted to reflect light incident on its side face.

Preferably, the channel is further adapted to receive a camera.

Preferably, the channel is adapted to receive a fibre optic or L.E.D light source.

Preferably, the light source emits light from a position at or near the transparent end face.

The present invention will now be described by way of example only with reference to the accompanying drawings in which:

FIGS. 9a to 9f illustrate an alternative light source or image capture device, various optical elements thereof, and the effects of the optical elements.

Figure 1:
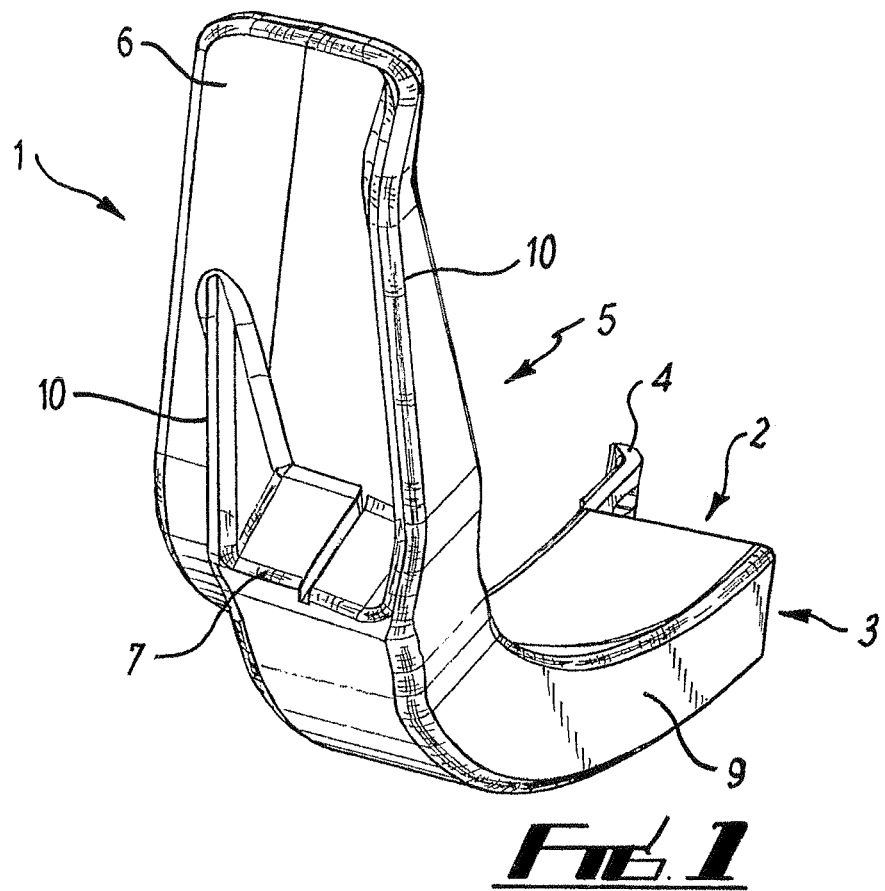
FIG. 1 is a perspective view of a first embodiment of the present invention.

FIG. 1 shows a blade 1 comprising an opening 2 and a hilt 3 having coupling means 4 for connecting the sheath type blade 1 to a laryngoscope, a blade end 5 having a blade tip 6.

The blade 1 contains a channel 9 which extends from the hilt 3 to the end face 7. The end face supports 10 are provided either side of the end face to improve the structural strength of the blade. The channel 9 is suitable for insertion of an image capture and/or an illumination device.

Figure 2:
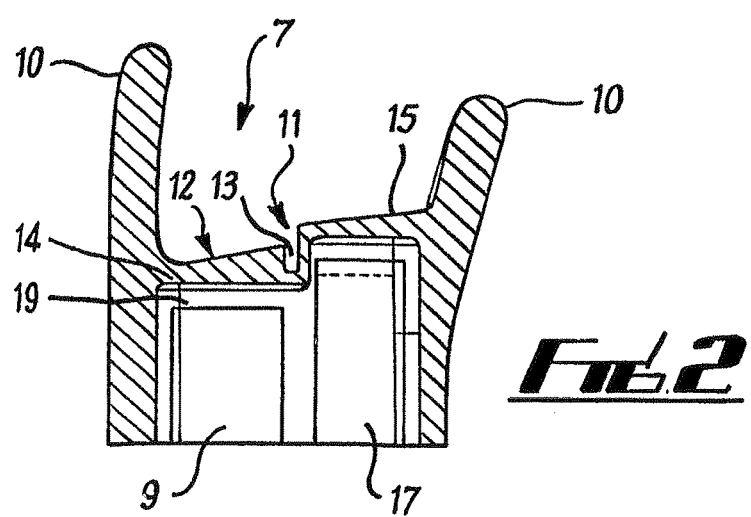
FIG. 2 is a cross-sectional view of the embodiment of FIG. 1.

FIG. 2 is a cross-sectional view of the end face 7. The end face contains an optical element 11 adapted to receive light from a light source 17. The optical element 11 comprises a prism 15 and is bounded by a gap or channel 13 which separates the optical element 9 from a second optical element 12 adapted to receive reflected light from the throat area (or other area of interest) of a patient and to transmit this light to a camera 19.

In this example of the present invention prisms 14 and 15 produce different degrees of refraction as a result of their different shapes.

In use, the first embodiment of the present invention is provided with a light source 17 and a camera 19. The light source 17 and camera 19 are inserted into the channel 9 and positioned at or near the end face 7. When a laryngoscope containing a sheath blade 1 as shown in FIG. 1 is in use, the light source 17 and camera 19 are switched on such that light may be transmitted down the throat of the patient for the reflected light to provide a signal which can display on a screen the area in which the laryngoscope blade is situated. This allows the physician to more accurately position the laryngoscope.

By modifying the end face 7, the present invention reduces the amount of light from the light source that leaks directly into the camera (ambient light) and increases the amount of light that is reflected from the throat area of the patient. In addition, the prisms 15 and 14 correct the direction of the transmitted and received light signals.

In this example the small degree of castellation is used to position the area from Which the light is omitted from the end face 7 in front of the area where reflected light is received by the camera 19. In addition, the optical element 11 is bounded by a gap or channel 13 which reduces the level of transmission of light across the front of the camera.

Figure 3:
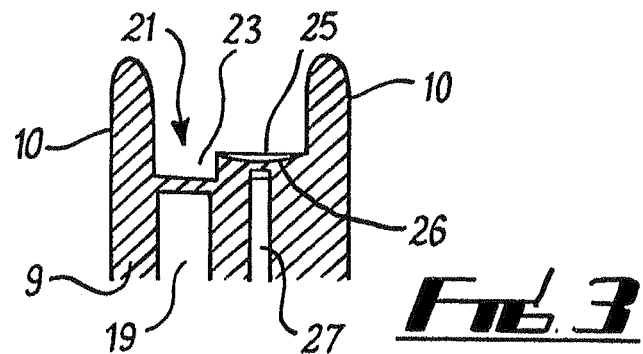
FIG. 3 is a cross-sectional view of the end face area of a second embodiment of the present invention.

FIG. 3 shows a second, embodiment of the present invention in which the end face 21 comprises a castellation 23, a narrow light source 27 and a camera 19. In this example, the narrow light source 27 is provided along with an optical element 25 comprising a lens 26 which causes the narrow beam to diverge and which maximises the amount of light that is incident upon the area of interest within the patient.

The combination of having the light source situated in front of the camera 19 and the use of a light source which provides a thin or narrow beam of light reduces the amount of ambient or back scattered light incident on the camera and increases the amount of reflected light incident upon the camera 19.

Figure 4:
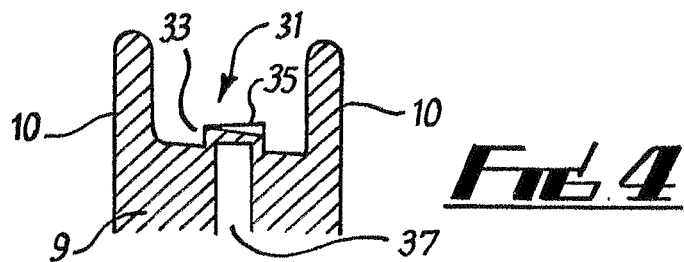
FIG. 4 is a cross-sectional view of the end face area of a third embodiment of the present invention.

FIG. 4 shows a third embodiment of the present invention in which the end face 31 comprises a castellated section 33 which, in this example, has the light source set in front of the remainder of the end face but substantially in the centre of the end phase. In this example of the present invention a camera is not present.

This embodiment of the present invention is designed to allow the direct visual inspection of the area of interest in the patient without the use of a camera. It has been found that the problem of ambient and/or backscattered light is important when a physician is attempting to directly observe the position of a laryngoscope blade as the ambient light makes it more difficult to correctly identify parts of the throat and voice box. By offsetting the position of the light source in front of the remainder of the end face 31, the level of ambient light that his viewed by the physician is reduced and the view improved.

Figure 5:
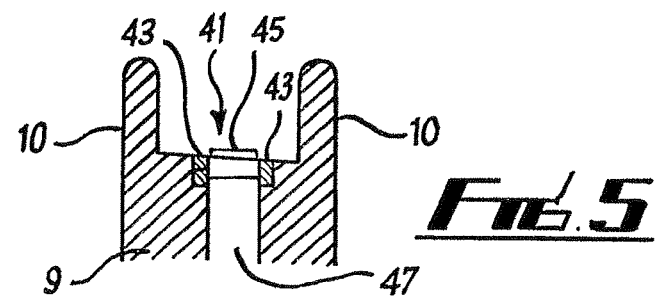
FIG. 5 is a cross-sectional view of the end face area of a fourth embodiment of the present invention.

FIG. 5 shows a fourth embodiment of the present invention in which the end face 41 is substantially flat except for the presence of an optical element 45. The end face is provided with the light absorbing barrier 43 which prevents light from the light source from entering the channel 9. The optical element 45 is positioned in front of the light source and is used to bend and/or expand the beam on exit from the end face 41.

In a further embodiment of the present invention the absorbing barrier 43 may be replaced by a barrier that reflects light internally such that light is not transmitted into the channel but reflected back toward the end face for transmission into the patient.

Figure 6:
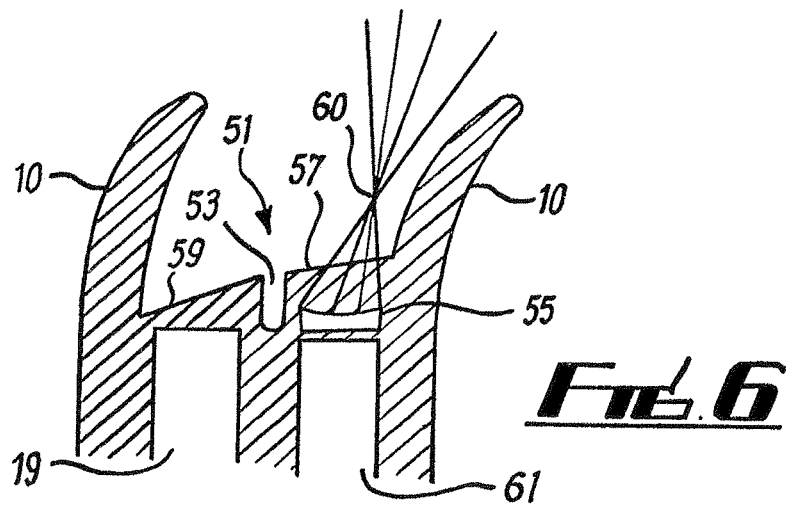
FIG. 6 is a cross-sectional view of the end face area of a fifth embodiment of the present invention.

FIG. 6 shows another embodiment of the present invention in which the end face 51 is provided with a channel or gap 53, a converging lens 55 positioned in front of the light source 61, and a camera prism positioned in front of the camera 19.

In this example of the present invention, the level of ambient or scattered light that effects the signal received by the camera 19 is produced by using a converging lens that focuses the light to a point 60 beyond the end face 51 with the beam subsequently diverging to maximise the amount of light incident upon the area of interest in the patient.

It will be noted that the curvature of the lens and therefore the degree of convergence or divergence that is required will be assessed on the basis of the distance between the end face 51 and the blade tip 6 (FIG. 1) along with the estimated distance from the blade tip 6 to the voice box of a patient.

FIGS. 7a to 7e show cross-sectional views of alternative end faces 107 (corresponding to end face 7 in FIG. 1). The end face contains an optical element 111 adapted to receive and transmit light from a light source 121. The optical element 111 is separated into two parts to prevent light from the light source 121 scattering through the end face 107.

Figure 7A:
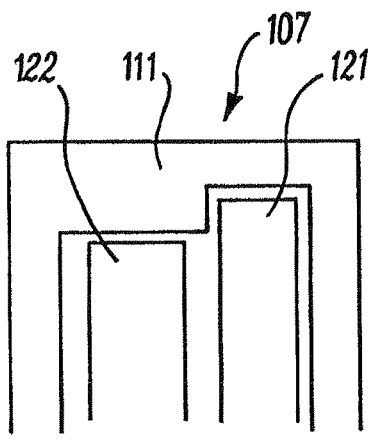
FIGS. 7a to 7e are cross-sectional views of the alternative end faces of the embodiment of FIG. 1.
Figure 7B:
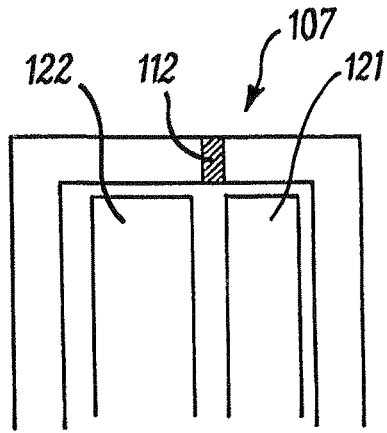
Figure 7C:
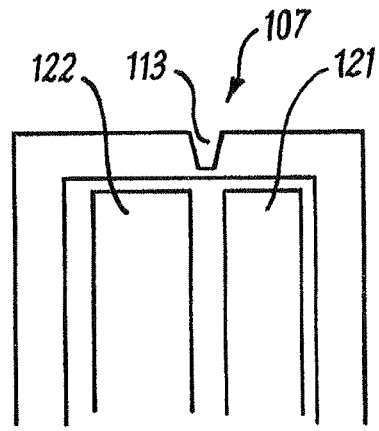

In FIG. 7a the separation is achieved by a castellation feature 111 which positions the light source 121 in front of the image capture device. In FIG. 7b the separation is achieved by separator element 112, whereas in FIG. 7c the separation is achieved by an air gap separation 113.

Figure 7D:
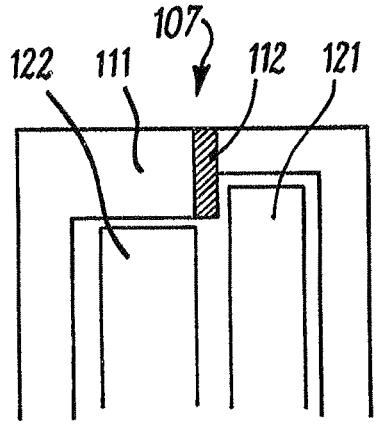
Figure 7E:
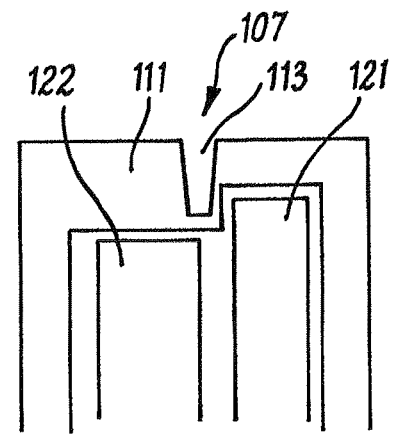

In FIG. 7d and FIG. 7e the separation is achieved by a combination of the castellation feature 111 and either the separator element 112 or the air gap separator 113, respectively.

Figure 8A:
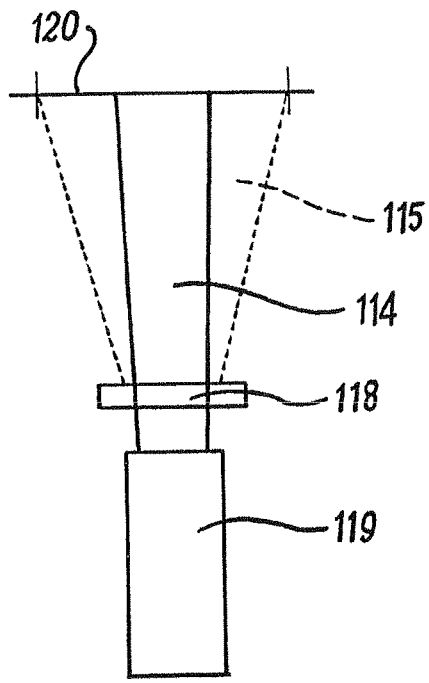
FIGS. 8a to 8c illustrate a light source or image capture device and various optical elements thereof.
Figure 8B:
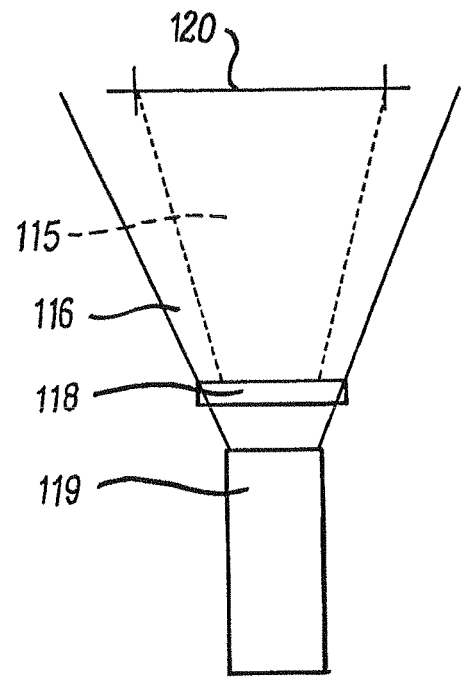

FIG. 8a and FIG. 8b illustrate a light source or image capture device 119 configured to transmit or receive light through an optical element 118. In FIG. 8a, the natural beam of light 114 transmitted or received is narrower than an optimal beam 115 as required to illuminate a target 120. In FIG. 8a, the natural beam of light 116 transmitted or received is wider than the optimal beam 115. In FIG. 8a, substantial areas of the target 120 are not illuminated or imaged. In FIG. 8b, the illumination or imaging of the target 120 is inefficient as a substantial amount of the illumination or image falls outwith the target 120.

Figure 8C:
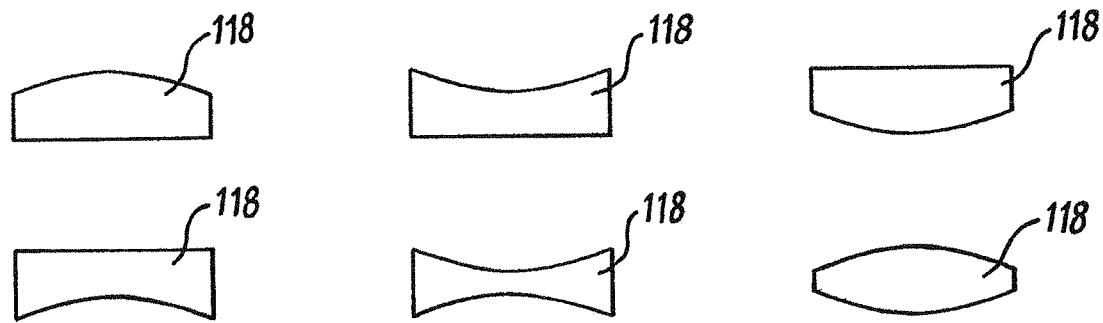

In order to achieve the optimal beam 115, the shape and size of the beam of light 114,116 transmitted to or received from the target 120 can be manipulated by the optical element 118 which may take the form of one of the lenses illustrated by FIG. 8c. These lenses may cause the beam of light to tend to converge or diverge towards the optimal beam 115.

FIG. 9a and FIG. 9b illustrate an alternative light source or image capture device 119 configured to transmit or receive light through an optical element 118. In this case the target 120 is offset from the light source or image capture device 119.

In FIG. 9a, the natural beam of light 114 transmitted or received is narrower than the optimal beam 117 as required by the offset target 120. In FIG. 9b, the natural beam of light 116 transmitted or received is wider than the optimal beam required by the offset target 120.

In order to achieve the optimal beam 117, the shape and size, of the beam of light 114,116 transmitted to or received from the offset target 120 can be manipulated by the optical element 118 which may take the form of a prism or a combined prism and lens such as those illustrated by FIG. 9c.

FIG. 9d illustrates the effect of the narrow natural beam 114 with respect to the offset target 120, and FIG. 9e illustrates the effect of the wide natural beam 116 with respect to the offset target 120. Substantial areas of the offset target 120 are not illuminated or imaged by the narrow natural beam 114, and importantly a significant area of the centre of the offset target are not illuminated or imaged. The illumination or imaging of the target 120 by the wider natural beam 116 is inefficient as a substantial amount of the illumination or image falls outwith the offset target 120, nevertheless, a significant area of the offset target is not illuminated or imaged.

FIG. 9f illustrates the result of correction of the natural beam 114,116 using an optical element 118 which may be selected from those illustrated in FIG. 9c or a combination thereof. The shaping of the natural beam 114,116 is such that a substantially rectangular shape is achieved, resulting in a more efficient use of light.

Figure 10A:
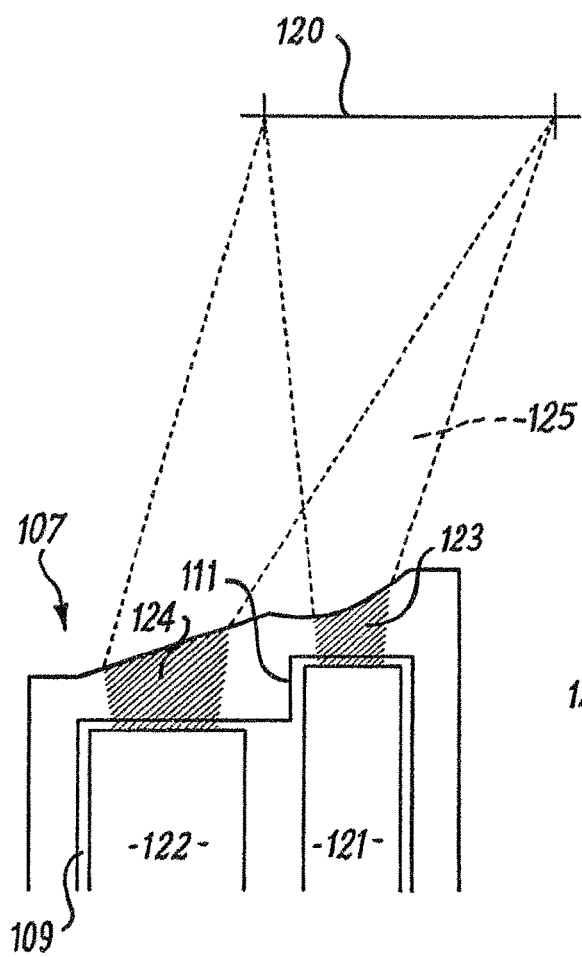
FIGS. 10a and 10b illustrate cross-sectional views of embodiments of the present invention incorporating the optical elements.
Figure 10B:
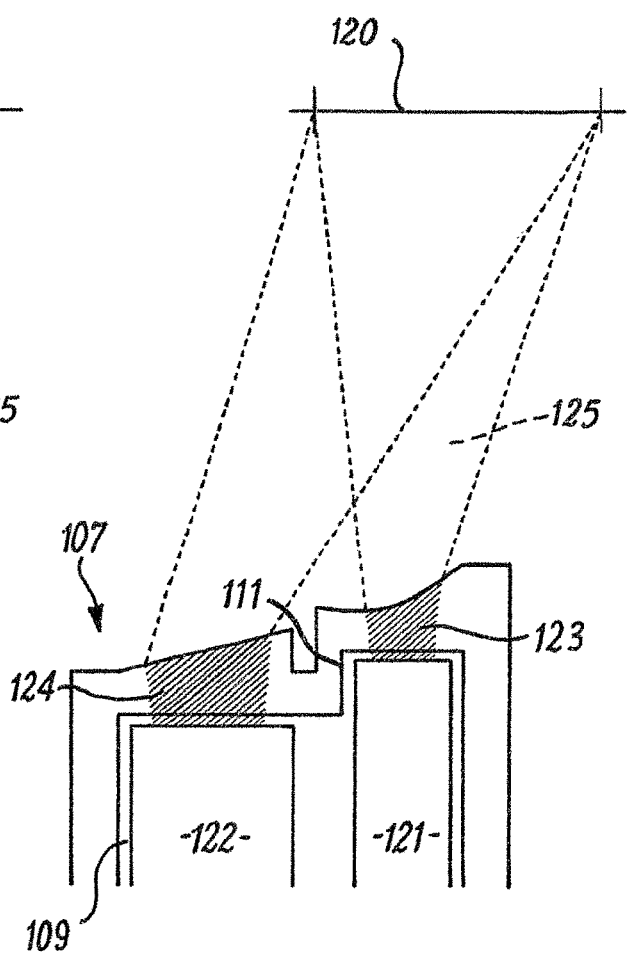

FIG. 10a and FIG. 10b illustrate cross-sectional views of the end face of embodiments of the present invention incorporating optical elements for improved imaging of an offset target 120.

A light source 121 and an image capture device 122 are inserted into the channel 109 which leads to the end face 107. The end face 107 comprises two separate optical elements, one for light transmission 123 and one for image capture 124. The optical elements 123,124 are separated by a castellation feature 111 which prevents scattering of light from the light source 121 into the image capture device 122.

The optical element for image capture 124 takes the form of a prism to collect light from the offset target 120. The optical element for the light source 123 takes the form of a lens and a prism to manipulate the shape and size of the light field 125 and direct it to the offset target 120. In FIG. 10b, the optical elements 123,124 are further separated by an air gap separator, further reducing any scatter from the light source 121 to the image capture device 122.

The present invention provides improvements in and relating to sheath type laryngoscopes by reducing the amount of scattered or ambient light that is received by a camera or directly received by the physician when viewing an area of interest in a patient. The present invention also assists with the correction of the beam direction and shape.

A preferred embodiment spaces apart the light source and the image capture means by way of a light stopping barrier and/or a castellation at the window area of the sheath. In the present invention the direction and shape of the illumination coming from the light source within the sheath is corrected so as to illuminate the desired area of the anatomy. In a preferred embodiment this is achieved by way of a prism and an angled lens which project a rectangular beam of light, at an angle, to suit that of the image capture means or display monitor.

Improvements and modifications may be incorporated herein without deviating from the scope of the invention as defined by the appended claims.

What is claimed is:
1. A laryngoscope blade comprising:
   a sheath forming a channel extending at least partially through the laryngoscope blade and configured to receive a light source and a camera and wherein the sheath is configured to cover the light source and the camera such that, in use, the light source and the camera are protected from contact with a patient, the channel having an opening disposed adjacent to a proximal end of the blade and terminating in an external end cap through which light from the light source is transmitted, wherein the external end cap comprises a prism producing a degree of refraction such that the throat area in which the blade is situated is visible to the camera, wherein the external end cap comprises a stepped interior surface wherein the prism is disposed within a first step of the stepped interior surface that is distal to a second step through which the camera is configured to receive the light;
   an elongated surface extending distally and laterally away from the external end cap to form a blade tip, wherein the blade tip is separated from the external end cap by the elongated surface; and
   end face supports extend from the external end cap to the elongated surface to provide strength to the laryngoscope blade.

2. The laryngoscope blade of claim 1, wherein the prism is configured to focus the light on a point positioned between the blade tip and the external end cap.

3. The laryngoscope blade of claim 1, wherein the prism is configured to redirect a beam of the light towards an offset target offset from an axis of the channel.

4. The laryngoscope blade of claim 1, wherein the prism is configured to redirect a beam of the light toward a wall or surface of the blade tip or towards a target positioned past the blade tip.

5. The laryngoscope blade of claim 1, wherein the external end cap is at least partially transparent.

6. The laryngoscope blade of claim 1, wherein the stepped interior surface comprises a distal portion and a proximal portion, and wherein the prism is in the distal portion.

7. The laryngoscope blade of claim 1, wherein an exterior surface of the external end cap is coupled to a side wall of the laryngoscope blade, wherein the side wall extends from a distal end of the channel toward the blade tip along at least a portion of the elongated surface, and wherein the side wall is orthogonal to the elongated surface.

8. The laryngoscope blade of claim 1, wherein the stepped interior surface opposes an exterior surface of the external end cap, wherein the exterior surface is not stepped.

9. The laryngoscope blade of claim 8, wherein the exterior surface is a planar surface extending between opposing side walls of the channel.

10. The laryngoscope blade of claim 1, wherein the stepped interior surface comprises a distal portion and a proximal portion, and wherein the proximal portion is longer than the distal portion across a cross-section of the channel.

11. The laryngoscope blade of claim 1, wherein the external end cap is transparent along the stepped interior surface.

12. The laryngoscope blade of claim 1, wherein the elongated surface extends from an inner curve of the channel.

13. The laryngoscope blade of claim 1, wherein the blade tip is wider than the channel.

14. A laryngoscope comprising:
a laryngoscope body;
a light source and a camera coupled to the laryngoscope body; and a laryngoscope blade coupled to the laryngoscope body, the laryngoscope blade forming a channel extending at least partially through the blade and configured to receive the light source and the camera, the channel terminating in an external end cap extending between side walls of the channel to close the channel at one end and through which light from the light source is transmitted, wherein the external end cap comprises a stepped interior surface, and wherein the external end cap is configured to direct light from the light source, and wherein the laryngoscope blade comprises an elongated surface extending longitudinally and laterally away from the external end cap to form a blade tip; and
end face supports extend from the external end cap to the elongated surface to provide strength to the laryngoscope blade.

15. The laryngoscope of claim 14, wherein the external end cap comprises a prism.

16. The laryngoscope of claim 15, wherein the prism is configured to focus the light on a point positioned between the blade tip and the external end cap.

17. The laryngoscope of claim 15, wherein the prism is configured to redirect a beam of the light towards an offset target offset from an axis of the channel.

18. The laryngoscope of claim 15, wherein the prism is configured to redirect a beam of the light toward a wall or surface of the blade tip.

19. The laryngoscope of claim 15, wherein the prism is configured to bend, expand, or redirect a beam of the light towards a target positioned past the blade tip.

20. The laryngoscope blade of claim 14, wherein an exterior surface of the external end cap is coupled to a side wall of the laryngoscope blade, wherein the side wall extends from a distal end of the channel toward the blade tip along at least a portion of the elongated surface, and wherein the side wall is orthogonal to the elongated surface.

21. The laryngoscope of claim 14, wherein the stepped interior surface is configured to transmit light from the light source through a first step and direct received light to the camera through a second step.

22. The laryngoscope of claim 14, wherein the elongated surface extends laterally away from the channel proximal of the external end cap.

* * * * *